US 6,680,318 B2
Jan. 20, 2004

(54) PIPERAZINOMETHYLBENZAMIDES AS DELTA-OPIOID RECEPTOR AGONISTS

(75) Inventors: William Brown, St. Laurent (CA); Christopher Walpole, St. Laurent (CA); Niklas Plobeck, St. Laurent (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/149,981

(22) PCT Filed: Dec. 15, 2000

(86) PCT No.: PCT/SE00/02562

§ 371 (c)(1),
(2), (4) Date: Oct. 21, 2002

(87) PCT Pub. No.: WO01/46174

PCT Pub. Date: Jun. 28, 2001

(65) Prior Publication Data

US 2003/0105110 A1 Jun. 5, 2003

(30) Foreign Application Priority Data

Dec. 20, 1999 (SE) ................................ 9904674

(51) Int. Cl.$^7$ .................... A61K 31/496; C07D 405/06; C07D 405/14

(52) U.S. Cl. ............................ 514/253.11; 514/254.07; 514/254.11; 544/364; 544/366; 544/370; 544/376

(58) Field of Search ................. 544/364, 376, 544/366, 370; 514/253.11, 254.11, 254.07

(56) References Cited

U.S. PATENT DOCUMENTS

| | | | |
|---|---|---|---|
| 3,940,386 A | 2/1976 | Szabo et al. | 260/240 |
| 5,574,159 A | 11/1996 | Chang et al. | 544/396 |
| 5,681,830 A | 10/1997 | Chang et al. | 514/85 |
| 5,807,858 A | 9/1998 | Chang et al. | 514/255 |
| 6,130,222 A | 10/2000 | Roberts et al. | 514/255.04 |

FOREIGN PATENT DOCUMENTS

| | | |
|---|---|---|
| DE | 24 31 178 | 1/1975 |
| DE | 29 00 810 | 7/1980 |
| EP | 0 133 323 | 2/1985 |
| EP | 0 166 302 | 1/1986 |
| EP | 0 283 310 | 9/1988 |
| EP | 0 289 227 | 11/1988 |
| FR | 2 696 744 | 4/1994 |
| GB | 2 076 403 | 12/1981 |
| GB | 2 210 366 | 6/1989 |
| JP | 7-138230 | 5/1995 |
| WO | WO 86/04584 | 8/1986 |
| WO | WO 91/07967 | 6/1991 |
| WO | WO 93/15062 | 8/1993 |
| WO | WO 95/04051 | 2/1995 |
| WO | WO/9723466 | 7/1997 |
| WO | WO 98/28270 | 7/1998 |
| WO | WO 98/28275 | 7/1998 |
| WO | WO 99/33806 | 7/1999 |

OTHER PUBLICATIONS

Burkey et al., Medline Abstract for Life Sci., vol. 62, pp.1531–1536 (1998).*
Nagase et al. Medline Abstract for Life Sci., vol. 68, pp. 2227–2231 (2001).*
Abstract for HU 217619. A corresponding English language PCT application is cited above as Reference AF1.
Abstract for HU 215847. A corresponding English language PCT application is cited above as Reference AG1.
Bilsky, et al., "Characterization of Enantiomers of (±)BW373U86 and Related Compounds: Highly Selective Non–Peptidic Delta Opioid Agonists," *Reg. Peptides* 54:25–26 (1994).
Bilsky, et al., "SNC 80, A Selective Nonpeptidic and Systemically Active Opioid ΔDelta Agonist," *J. Pharmacol. Exper. Therap.* 273:359–366 (1995).
Calderon, et al., "Probes for Narcotic Receptor Mediated Phenomena. 19. Synthesis of (+)–4–[(αR)–α–((2S,5R )–4–Allyl–2,5–Dimethyl–1–Piperazinyl)–3–Methoxybenzyl]– N,N–Diethylbenzamide (SNC 80): A Highly Selective, Nonpeptide δ Opioid Receptor Agonist," *J. Med. Chem.* 37:2125–2128 (1994).
Calderon, et al., "Probes for Narcotic Receptor Mediated Phenomena. 23. Synthesis, Opioid Receptor Binding, and Bioassay of the Highly Selective δ Agonist (+)–4–[(αR)–α–((2S,5R)–4–Allyl–2,5–Dimethyl–1–Piperazinyl)–3–Methoxybenzyl]–N,N –Diethylbenzamide (SNC 80) and Related Novel Nonpeptide α Opioid Receptor Ligands," *J. Med. Chem.* 40:695–704 (1997).
Chang, et al., "A Novel, Potent and Selective Nonpeptidic βOpioid Receptor Agonist BW373U86," *J. Pharmacol. Exper. Therap.* 267:852–857 (1993).
Greene, "Protective Groups in Organic Synthesis," pp. 267–268 and 331 (1981).

(List continued on next page.)

*Primary Examiner*—Emily Bernhardt
(74) *Attorney, Agent, or Firm*—Michael A. Sanzo; Fitch, Even, Tabin & Flannery

(57) ABSTRACT

The present application is directed to compounds having the general formula:

and to the use of these compounds in therapeutic methods.

20 Claims, No Drawings

OTHER PUBLICATIONS

Katrizky, et al., "Benzotriazole–Mediated Arylalkylation and Heteroarylalkylation," *Chem. Soc. Rev.* 23:363–442 (1994).

Kingsbury, et al., "Synthesis of Structural Analogs of Leukotriene $B_4$ and Their Receptor Binding Activity," *J. Med. Chem.* 36:3308–3320 (1993).

Lopez, et al., "Exploring the Structure–Activity Relationships of [1–(4–tert–Butyl–3'–Hydroxy)Benzhydryl–4–Benzyl-piperazine] (SL–3111), a High–Affinity and Selective δ–Opioid Receptor Nonpeptide Agonist Ligand," *J. Med. Chem.* 42:5359–5368 (1999).

Plobeck, et al., "New Diarylmethylpiperazines as Potent and Selective Nonpeptidic δ Opioid Receptor Agonists with Increased In Vitro Metabolic Stability," *J. Med. Chem.* 43:3878–3894 (2000).

Suggs, et al., "Facile Synthesis of 8–Substituted Quinolines," *J. Org. Chem* 45:1514–1515 (1980).

Takemori, et al., "Selective Natrexone–Derived Opioid Receptor Antagonists," *Annu. Rev. Pharmacol. Toxicol.* 32:239–269 (1992).

Zhang, et al., Probes for Narcotic Receptor Mediated Phenomena. 26. Synthesis and Biological Evaluation of Diarylmethylpiperazines and Diarylmethylpiperidines as Novel, Nonpeptidic δ Opioid Receptor Ligands, *J. Med. Chem.* 42:5455–5463 (1999).

Dialog Abstract for FR 2 696 744, Reference AH3 below.
Dialog Abstract for DE 24 31 178, Reference AI3 above.
Dialog abstract for DE 29 00 810, Reference AJ3 above.
Dialog abstract for JP 7–128230, Reference AK3 above.
Abstract No. 8843b for JP 7–138230, Reference AK3 above, *Chemical Abstracts 124*:938 (1996).

* cited by examiner

PIPERAZINOMETHYLBENZAMIDES AS DELTA-OPIOID RECEPTOR AGONISTS

CROSS REFERENCE TO RELATED APPLICATIONS

The present application represents U.S. national stage of international application PCT/SE00/02562, which had an international filing date of Dec. 15, 2000 and which was published in English under PCT Article 21(2) on Jun. 28, 2001. The international application claims priority to Swedish application 9904674-0, filed on Dec. 20, 1999.

FIELD OF THE INVENTION

The present invention is directed to novel compounds, to a process for their preparation, their use and pharmaceutical compositions comprising the novel compounds. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors ($\mu$, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., *Journal of Pharmacology and Experimental Therapeutics*, 273(1), pp. 359–366 (1995)). There is however still a need for selective δ-agonists having not only improved selectivity, but also an improved side-effect profile.

Thus, the problem underlying the present invention was to find new analgesics having improved analgesic effects, but also with an improved side-effect profile over current $\mu$ agonists, as well as having improved systemic efficacy.

Analgesics that have been identified and are existing in the prior art have many disadvantages in that they suffer from poor pharmacokinetics and are not analgesic when administered by systemic routes. Also, it has been documented that preferred δ agonist compounds, described within the prior art, show significant convulsive effects when administered systemically.

We have now found that certain compounds not specifically disclosed by, but included within the scope of WO 98/28270, exhibit surprisingly improved δ-agonist properties and in vivo potency relative to compounds disclosed in WO98/28270, when administered systemically. The compounds of the present invention exhibit significant and unexpected increased levels of delta receptor agonism and metabolic stability.

OUTLINE OF THE INVENTION

The novel compounds according to the present invention are defined by the formula I

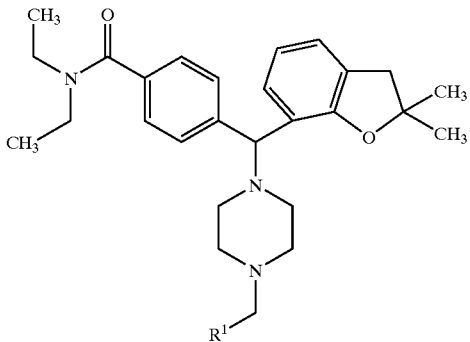

I wherein
R$^1$ is selected from
(i) phenyl;
(ii) pyridinyl

(iii) thiophenyl

(iv) furanyl

(v) imidazolyl

(vi) triazolyl

where each R$^1$ phenyl ring and R$^1$ heteroaromatic ring may optionally and independently be further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems.

Within the scope of the invention are also pharmaceutically acceptable salts of the compounds of the formula I, as well as isomers thereof.

When the phenyl ring and the heteroaromatic ring(s) are substituted, the preferred substituents are selected from anyone of $CF_3$, methyl, iodo, bromo, fluoro and chloro.

In a preferred embodiment of the invention, the compounds of formula I are present as the (+)-enantiomer, or as the (−)-enantiomer.

By "isomers" we mean compounds of the formula I, which differ by the position of their functional group and/or orientation. By "orientation" we mean stereoisomers, diastereoisomers, regioisomers and enantiomers.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety, urinary incontinence, various mental illnesses, cough, lung oedema, various gastrointestinal disorders, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (eg. amnesia, analgesia, muscle relaxation and sedation). Included in this combination are inhaled anaesthetics, hypnotica, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

Also included within the scope of the present invention, is any novel intermediate as described in Scheme I hereinafter useful in the synthesis of compounds of formula I above.

Methods of Preparation

The compounds according to the present invention may be prepared by following the synthetic procedure described in Scheme I below. This known procedure is described in Katritsky, A. R., Laji, X. *Chem. Soc. Rev.*, pp. 363–373 (1994), which is hereby incorporated by reference.

Scheme 1

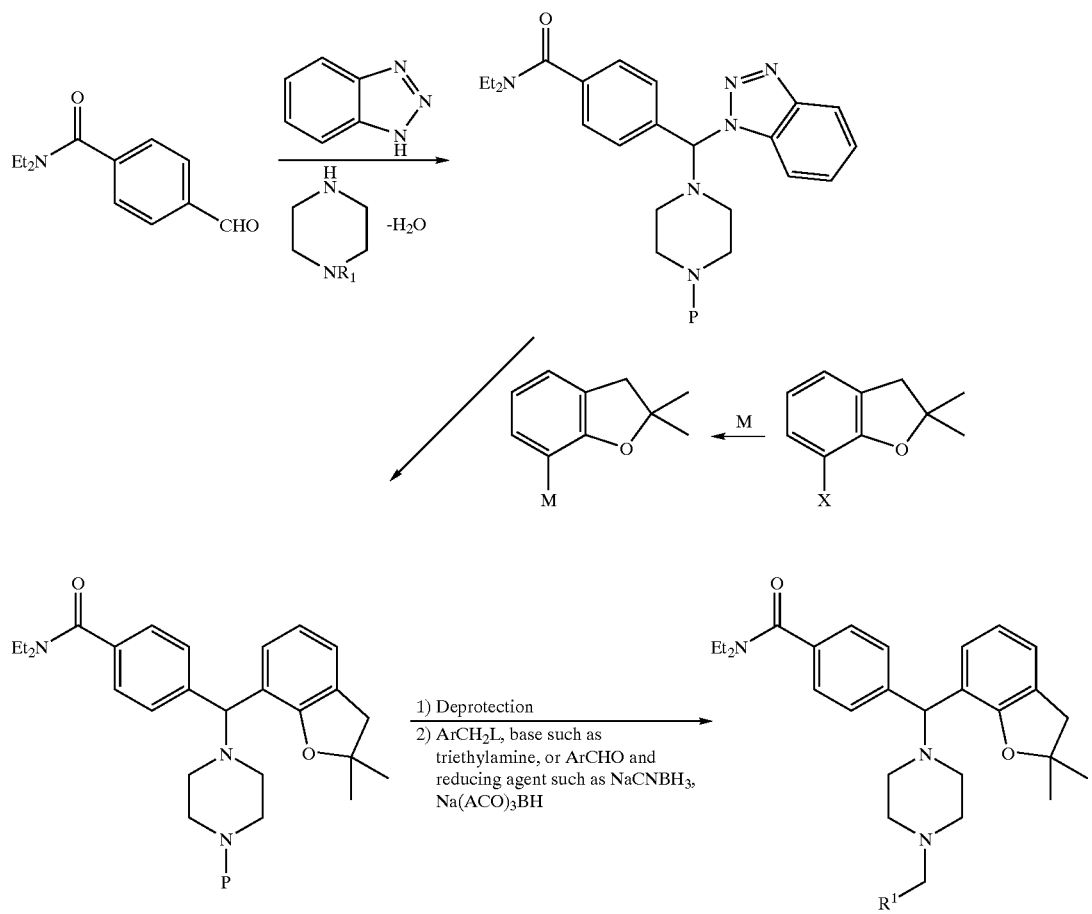

P = a protecting group such as Bn, Boc, CBz
M = Li, Mg, Zn
X = Br, I
L = Cl, Br, OMs, OTs, I
$R^1$ = as defined in formula (I) above

EXAMPLES
The invention will now be described in more detail by the following Examples, which are not to be construed as limiting the invention.
The compounds according to Examples 1–3 were prepared by following the synthetic procedure described in Scheme I below.
Scheme 1
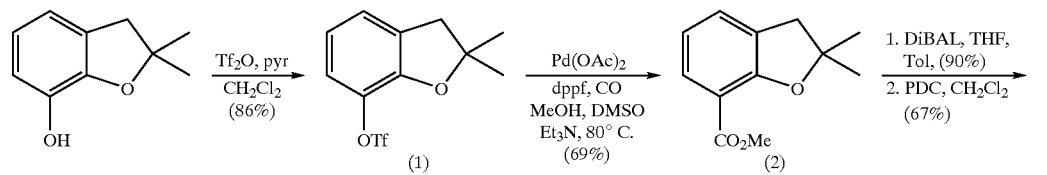
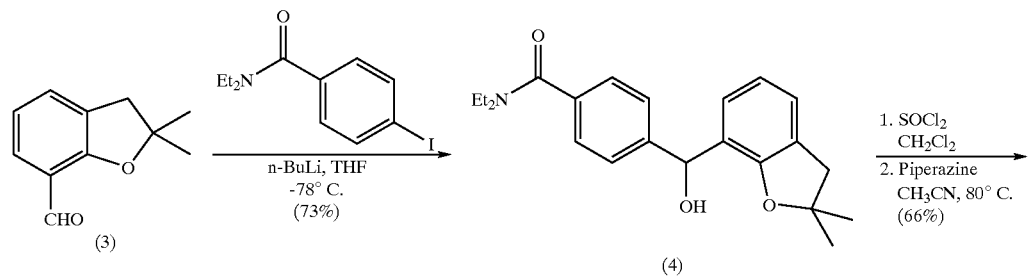
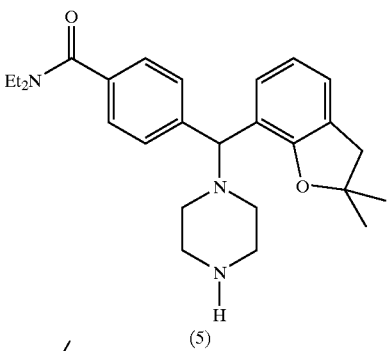

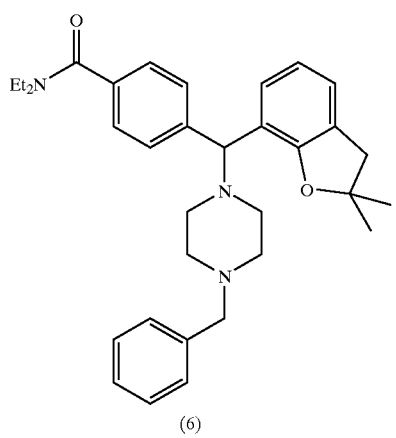

(6)

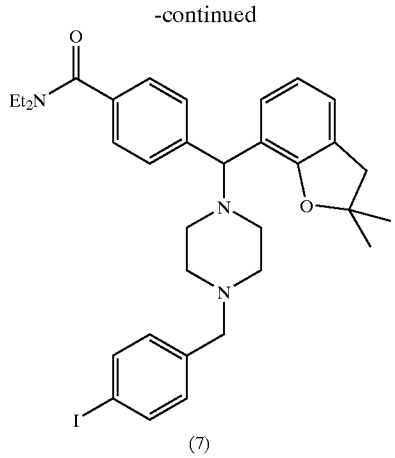

(7)

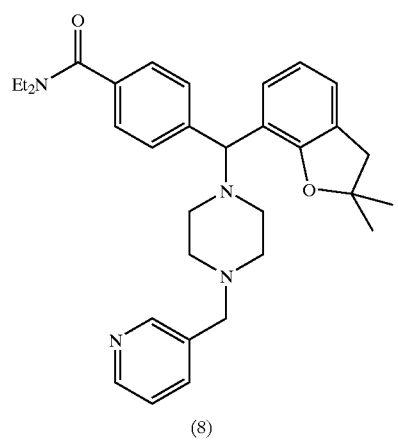

(8)

Example 1
Preparation of 4-[(4-benzyl-1-piperazinyl)(2,2-dimethyl-2,3-dihydro-1-benzofuran-7-yl)methyl]-N,N-diethylbenzamide Dihydrochloride (Compound 6)

(i) Preparation of 2,2-Dimethyl-2,3-dihydro-1-benzofuran-7-yl Trifluoromethanesulfonate (Compound 1)

2,2-dimethyl-2,3-dihydro-1-benzofuran-7-ol (19 g, 0.11 mol) and pyridine (18 mL, 0.23 mol) was dissolved in $CH_2Cl_2$ at 0° C. Triflic anhydride (23 mL, 0.14 mol) was added dropwise. After stirring 1 h at 25° C. the mixture was diluted with $CH_2Cl_2$ and washed with HCl (aq.), dried (Mg $SO_4$) and evaporated in vacuo.

Yield 32 g (96%) of compound 1, which did not need purification but was used directly in the following step.

$^1$H NMR (CDCl$_3$) δ 1.50 (s, 6H), 3.09 (s, 2H), 6.81 (m, 1H), 7.03 (m, 1H), 7.11 (m, 1H), MS (EI) m/e 296, 163, 135, 107.

(ii) Preparation of Methyl 2,2-dimethyl-2,3-dihydro-1-benzofuran-7-carboxylate (Compound 2)

Compound 1 prepared in the previous step above (32 g, 0.11 mol) was dissolved in DMSO (200 mL), MeOH (100 mL) and Et$_3$N (34 mL, 0.25 mol). Carbon monoxide was passed through the solution 2–3 min, then palladium acetate (0.24 g) and dppf (1.1 g) was added and the mixture heated at 70° C. under CO atmosphere. After 4 h, more palladium acetate (0.10 g) and dppf (0.50 g) was added. After 12 h, EtOAc and water was added and the organic phase was washed with HCl (aq.), brine, dried (MgSO$_4$) and evaporated. chromatography on silica (0–20% EtOAc in heptane) gave 12 g (52%) of compound 2.

$^1$H NMR (CDCl$_3$) δ 1.52 (s, 6H), 3.00 (s, 2H), 3.88 (s, 3H), 6.82 (m, 1H), 7.27 (m, 1H), 7.70 (m, 1H). MS (EI) m/e 206, 174, 159, 146, 131.

(iii) Preparation of 2,2-Dimethyl-2,3-dihydro-1-benzofuran-7-carbaldehyde (Compound 3)

Compound 2 (5.0 g, 24 mmol) was dissolved in toluene (100 mL) and DIBAL in toluene (33 mL, 1.5 M, 50 mmol) was added at −78° C. under nitrogen atmosphere. After 30 min, the reaction was worked up by addition of HCl (aq.), the organic phase was dried (MgSO$_4$) and evaporated in vacuo. The residue was dissolved in CH$_2$Cl$_2$ (50 mL) and finely ground pyridinium dichromate (PDC) (11 g, 29 mmol) was added in portions. The mixture was heated at 40° C. and portions of PDC (1 g) was added until reaction was complete. Dilution with heptane, filtering through silica and evaporation gave a crude product which was purified by chromatography on silica (0–20% EtOAc in heptane) to give compound 3 (3.3 g, 19 mmol, 67% from compound 2.

$^1$H NMR (CDCl$_3$) δ 1.54 (s, 6H), 3.03 (s, 2H), 6.88 (m, 1H), 7.34 (m, 1H), 7.58 (m, 1H), 10.22 (s, 1H). MS (EI) m/e 176, 161, 147, 130.

(iv) & (v) Preparation of 4-[(2,2-dimethyl-2,3-dihydro-1-benzofuran-7-yl)(hydroxy)methyl]-N,N-diethylbenzamide (Compound 4) and 4-[(2,2-dimethyl-2,3-dihydro-1-benzofuran-7-yl)(1-piperazinyl)methyl]-N,N-diethylbenzamide (Compound 5)

N,N-Diethyl-4-iodobenzamide (compound I) (14 g, 47 mmol) was dissolved in THF (150 mL) and cooled to −78° C. under nitrogen atmosphere. n-BuLi (21 mL, 2.2 M solution in hexane, 47 mmol) was added dropwise. Stirring was continued for 30 min at −78° C. The aldehyde (compound 3) (4.1 g, 24 mmol) was added dropwise dissolved in THF (2 mL). NH$_4$Cl (aq.) was added after 30 min. After concentration in vacuo, extraction with EtOAc/water, drying (MgSO$_4$) and evaporation of the organic phase, the residue was purified by chromatography on silica to (compound 4) (6.1 g, 17 mmol). After treatment with SOCl$_2$ (1.5 mL, 20 mmol) in dry CH$_2$Cl$_2$ (200 mL) at 0 to 25° C. for 1 h, the solvent was evaporated in vacuo. The residue was dissolved in MeCN (100 mL) and reacted with piperazine (5.8 g, 68 mmol) at 80° C. for 12 h. After concentration in vacuo and chromatography on silica (0 to 15% MeOH in CH$_2$Cl$_2$, with 1% NH$_4$OH) gave (compound 5) (4.9 g, 11 mmol). Dihydrochloride made with HCl (aq) and lyophilization.

mp 130–40° C. (di HCl salt).

IR (KBr, v$_{max}$) 2982, 2722, 2481, 1628, 1450, 1371, 1292, 1140.

$^1$H NMR (CD$_3$OD) δ 1.1,1.2 (2m, 6H), 1.36, 1.43 (2s, 6H), 2.72 (m, 4H), 2.95 (m, 2H), 3.25 (m, 6H), 3.5 (m, 2H), 4.8 (s, 1H), 6.74–7.60 (m, 7H). Anal. (C$_{26}$H$_{35}$N$_3$O$_2$) C, H, N.

(vi) Preparation of the Title Compound 4-[(4-benzyl-1-piperazinyl)(2,2-dimethyl-2,3-dihydro-1-benzofuran-7-yl)methyl]-N,N-diethylbenzamide Dihydrochloride (Compound 6)

Compound 5 (0.62 g, 1.5 mmol) and triethylamine (0.41 mL, 2.9 mmol) was dissolved in MeCN (5 mL) and reacted with benzyl bromide (0.17 mL, 1.5 mmol) at 25° C. After 2 h a second portion benzyl bromide was added, and after 4 h the reaction was worked up by concentration in vacuo and chromatography on silica (0 to 10% MeOH in $CH_2Cl_2$) to give the title compound 6 (0.49 g, 0.95 mmol). Dihydrochloride made with HCl (aq) and lyophilization. MS (ES) 512.08 (MH+).

IR (NaCl, free amine, $v_{max}$) 2969, 2806, 2360, 1630, 1451, 1368, 1289, 1135 $cm^{-1}$.

$^1$H NMR ($CDCl_3$, free amine) δ 1.1, 1.2 (2m, 6H, amide-Me), 1.36, 1.46 (2s, 6H, Me2C), 2.5 (m, 8H, piperazine-H), 2.92 (m, 2H, ArCH2), 3.2, 3.5 (2m, amide-CH2), 3.51 (s, 2H, ArCH2N), 4.62 (s, 1H, Ar2CH), 6.72–7.52 (m, 7H, Ar—H). Anal. ($C_{33}H_{41}N_3O_2$×3.4 HCl) C, H; N: calcd, 6.61; found, 7.19.

Example 2

Preparation of 4-{(2,2-dimethyl-2,3-dihydro-1-benzofuran-7-yl)[4-(4-iodobenzyl)-1-piperazinyl]methyl}-N,N-diethylbenzamide Dihydrochloride (Compound 7)

Procedure as for compound 6. Compound 5 (0.12 g, 0.29 mmol) was reacted with 4-iodobenzyl bromide (96 mg, 0.32 mmol) for 48 h to give the title compound 7 (56 mg, 88 μmol).

MS (ES) 638.24 (MH+). IR (NaCl, free amine, $v_{max}$) 2969, 2810, 1630, 1451, 1288, 1135, 1007 $cm^{-1}$.

$^1$H NMR ($CDCl_3$, free amine) δ 1.1, 1.2 (2m, 6H, amide-Me), 1.36, 1.45 (2s, 6H, Me2C), 2.4 (m, 8H, piperazine-H), 2.94 (m, 2H, ArCH2), 3.2, 3.5 (2m, amide-CH2), 3.43 (s, 2H, ArCH2N), 4.62 (s, 1H, Ar2CH), 6.73 (m, 1H, Ar—H), 6.94 (d, J=7.3 Hz, 1H, ArH), 7.05 (d, J=8.0 Hz, 2H, ArH), 7.19 (d, J=6.6 Hz, 1H, ArH), 7.25 (d, J=8.0 Hz, 2H, ArH), 7.48 (d, J=8.0 Hz, 2H, ArH), 7.61 (d, J=8.0 Hz, 2H, ArH). Anal. ($C_{26}H_{37}Cl_2N_3O_2$) C, H, N.

Example 3

Preparation of 4-{(2,2-dimethyl-2,3-dihydro-1-benzofuran-7-yl)[4-(3-pyridinylmethyl)-1-piperazinyl]methyl}-N,N-diethylbenzamide Dihydrochloride (Compound 8)

Compound 5 (0.20 g, 0.47 mmol) was dissolved in MeOH (2 mL) with 3-pyridine carboxaldehyde(90 μL, 0.95 mmol) and HOAc (3 μL, 50 μmol). Sodium cyanoborohydride (60 mg, 0.95 mmol) was added at 0° C. and reaction stirred 48 h at 25° C. Reaction was worked up by concentration in vacuo, extraction ($CH_2Cl_2/K_2CO_3$(aq)) and chromatography on silica (0 to 10% MeOH in $CH_2Cl_2$) to give the title compound δ (82 mg, 0.16 mmol). Dihydrochloride made with HCl (aq) and lyophilization.

MS 513.25 (MH+). IR (NaCl, free amine, $v_{max}$) 2970, 2808, 2360, 1631, 1452, 1425, 1290, 1135, 1096, 1009 $cm^{-1}$.

$^1$H NMR ($CDCl_3$, free amine) δ 1.1, 1.2 (2m, 6H, amide-Me), 1.36, 1.46 (2s, 6H, Me2C), 2.5 (m, 8H, piperazine-H), 2.94 (m, 2H, ArCH2), 3.2, 3.5 (2m, amide-CH2), 3.51 (s, 2H, ArCH2N), 4.64 (s, 1H, Ar2CH), 6.72–7.66 (m, 9H, Ar—H), 8.44–8.54 (m, 2H, Ar—H). Anal. ($C_{32}H_{42}Cl_2N_4O_2$) C, H, N.

Example 4

Preparation of 4-{(2,2-dimethyl-2,3-dihydro-1-benzofuran-7-yl)[4-(2-pyridinylmethyl)-1-piperazinyl]methyl}-N,N-diethylbenzamide Ditrifuroacetae (Compound 9)

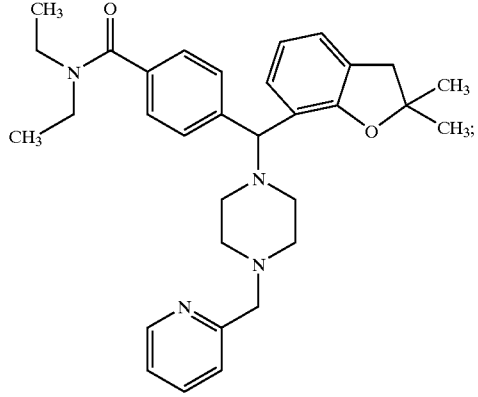

(9)

The title compound 9 was prepared by dissolving compound 5 (0.45 g, 0.98 mmol) in MeOH (10 mL) with 2-pyridine carboxaldehyde (110 μL, 1.18 mmol) and HOAc (3 μL, 50 μmol). Sodium cyanoborohydride (70 mg, 1.18 mmol) was added at 0° C. and reaction stirred 48 h at 25° C. Reaction was worked up by concentration in vacuo, extraction ($CH_2Cl_2/K_2CO_3$(aq)) and chromatography by reverse phase HPLC to give the title compound 9,461 mg(63%).

MS 513.04 (MH+).

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminium, calcium, lithium, magnesium, potassium, sodium, and zinc. Preferred pharmaceutically acceptable salts are the hydrochlorides, and bitartrates. The hydrochloride salts are particularly preferred.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Biological Evaluation

In vitro Model

Cell Culture

Human 293S cells expressing cloned human $\mu$, $\delta$, and $\epsilon$ receptors and neomycin resistance were grown in suspension at 37° C. and 5% $CO_2$ in shaker flasks containing calcium-free DMEM 10% FBS, 5% BCS, 0.1% Pluronic F-68, and 600 µg/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 µg/ml aprotinin, 10 µM bestatin, 10 µM diprotin A, no DTT). Aliquots of 100 µl (for µg protein, see Table 1) were added to iced 12×75 mm polypropylene tubes containing 100 µl of the appropriate radioligand (see Table 1) and 100 µl of test peptides at various concentrations. Total (TB) and nonspecific (NS) binding were determined in the absence and presence of 10 µM naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 µl MS-20 scintillation fluid/well.

Data Analysis

The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves. Biological data are reported below in Table 1.

TABLE 1

Summary of biological data.

| Example # | HDelta | HDelta EC50 | % EMAX | Rat Brain EC50 | % EMAX | Mouse Brain EC50 | % EMAX | MLM 10000 % rem. | MLM 100000 % rem. | RLM 10000 % rem. | RLM 100000 % rem. |
|---|---|---|---|---|---|---|---|---|---|---|---|
| 3 | 3.519 | 19.47 | 103.1 | 133.72 | 92.97 | | | | | | |
| 4 | 3.264 | 7.38 | 103.9 | 72.59 | 118.04 | 144.13 | 118.5 | 44.5 | 93 | 42.5 | 90.5 |

Receptor Saturation Experiments

Radioligand Kδ values were determined by performing the binding assays on cell membranes with the appropriate radioligands at concentrations ranging from 0.2 to 5 times the estimated Kδ (up to 10 times if amounts of radioligand required are feasable). The specific radioligand binding was expressed as pmole/mg membrane protein. Values of Kδ and $B_{max}$ from individual experiments were obtained from non-linear fits of specifically bound (B) vs. nM free (F) radioligand from individual according to a one-site model.

Determination of Mechano-Allodynia Using Von Frey Testing

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold} = 10^{(Xf+k\delta)}/10,000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% MPE = \frac{\text{Drug treated threshold (g)} - \text{allodynia threshold (g)}}{\text{Control threshold (g)} - \text{allodynia threshold (g)}} \times 100$$

Administration of Test Substance

Rats were injected (subcutaneously, intraperitoneally, or orally) with a test substance prior to von Frey testing, the time between administration of test compound and the von Frey test varied depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflexe is considered only when the following elements are present: the animal is not in movement; the lower back is slightly depressed; the plantar aspect of both paws is observable.

(i) Solutions Preparation

Acetic acid (AcOH): 120 μL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

What is claimed is:

1. A compound according to formula I:

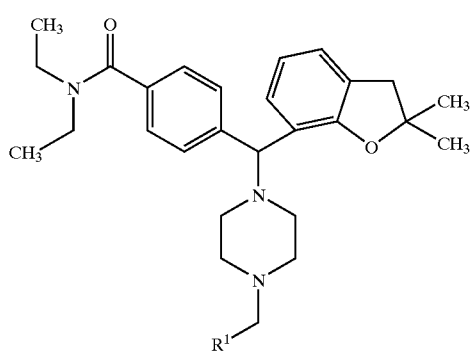

wherein
R¹ selected from:
(i) phenyl;
(ii) pyridinyl

(iii) thiophenyl

(iv) furanyl

(v) imidazolyl

(vi) triazolyl

where each R¹ phenyl ring and R¹ heteroaromatic ring may optionally and independently be further substituted by 1, 2 or 3 substituents selected from: a straight or branched $C_1$–$C_6$ alkyl, $NO_2$, $CF_3$, $C_1$–$C_6$ alkoxy, chloro, fluoro, bromo and iodo; wherein the substitutions on the phenyl ring and on the heteroaromatic ring may take place at any position on a ring system;
as well as pharmaceutically acceptable salts and stereoisomers thereof.

2. The compound of claim 1, wherein the optional substituent(s) on the aromatic or heteroaromatic ring(s) is selected from any one of $NO_2$, isobutyl, $CF_3$ methoxy, methyl or chloro.

3. A compound selected from any one of:
4-[(4-benzyl-1-piperazinyl)(2,2-dimethyl-2,3-dihydro-1-benzofuran-7-yl)methyl]-N,N-diethylbenzamide dihydrochloride (compound 6);
4-{(2,2-dimethyl-2,3-dihydro-1-benzofuran-7-yl)[4-(4-iodobenzyl)-1-piperazinyl]methyl}-N,N-diethylbenzamide dihydrochloride (compound 7);
4-{(2,2-dimethyl-2,3-dihydro-1-benzofuran-7-yl)[4-(3-pyridinylmethyl)-1-piperazinyl]methyl}-N,N-diethylbenzamide dihydrochloride (compound 8); and
4-{(2,2-dimethyl-2,3-dihydro-1-benzofuran-7-yl)[4-(2-pyridinylmethyl)-1-piperazinyl]methyl}-N,N-diethylbenzamide ditrifluroacetate (compound 9).

4. The compound of any one of claims 1–3, wherein said compound is present as the (+)-enantiomer.

5. The compound of any one of claims 1–3, wherein said compound is present as the (−)-enantiomer.

6. The compound of one of claims 1–3, wherein said compound is in the form of its hydrochloride, sulfate, tartrate or citrate salt.

7. A pharmaceutical composition comprising a compound according to any one of claims 1–3 as an active ingredient, together with a pharmacologically and pharmaceutically acceptable carrier.

8. A method of treating a subject for pain, comprising administering to said subject an effective amount of a compound according to any one of claims 1–3.

9. The compound of claim 1, wherein R¹ is phenyl, optionally substituted by 1, 2 or 3 substituents selected from: a straight or branched $C_1$–$C_6$ alkyl; $NO_2$, $CF_3$; $C_1$–$C_6$ alkoxy; chloro; fluoro; bromo; and iodo; wherein the substitutions may occur in any position on said phenyl.

10. The compound of claim 1, wherein R¹ is pyridinyl, optionally substituted by 1, 2 or 3 substituents selected from: a straight or branched $C_1$–$C_6$ alkyl; $NO_2$, $CF_3$, $C_1$–$C_6$ alkoxy; chloro; fluoro; bromo; and iodo; wherein the substitutions may occur in any position on said pyridinyl.

11. The compound of claim 1, wherein R¹ is thiophenyl, optionally substituted by 1, 2 or 3 substituents selected from: a straight or branched $C_1$–$C_6$ alkyl; $NO_2$; $CF_3$; $C_1$–$C_6$ alkoxy; chloro; fluoro; bromo; and iodo; wherein the substitutions may occur in any position on said thiophenyl.

12. The compound of claim 1, wherein R¹ is furanyl, optionally substituted by 1, 2 or 3 substituents selected from: a straight or branched $C_1$–$C_6$ alkyl; $NO_2$; $CF_3$; $C_1$–$C_6$ alkoxy; chloro; fluoro; bromo; and iodo; wherein the substitutions may occur in any position on said furanyl.

13. The compound of claim 1, wherein R¹ is imidazolyl optionally substituted by 1, 2 or 3 substituents selected from: a straight or branched $C_1$–$C_6$ alkyl; $NO_2$; $CF_3$; $C_1$–$C_6$ alkoxy; chloro; fluoro; bromo; and iodo; wherein the substitutions may occur in any position on said imidazolyl.

14. The compound of claim 1, wherein R¹ is triazolyl optionally substituted by 1, 2 or 3 substituents selected from: a straight or branched $C_1$–$C_6$ alkyl; $NO_2$; $CF_3$; $C_1$–$C_6$ alkoxy; chloro; fluoro; bromo; and iodo; wherein the substitutions may occur in any position on said triazolyl.

15. The compound of any one of claims 9–14, wherein said compound is present as the (+)-enantiomer.

16. The compound of any one of claims 1–3, wherein said compound is present as the (−)-enantiomer.

17. The compound of one of claims 9–14, wherein said compound is in the form of its hydrochloride, sulfate, tartrate or citrate salt.

18. A pharmaceutical composition comprising a compound according to any one of claims 9–14 as an active ingredient, together with a pharmacologically and pharmaceutically acceptable carrier.

19. A method of treating a subject for pain, comprising administering to said subject an effective amount of a compound according to any one of claims 9–14.

20. The method of claim 19, wherein said pain is neuropathic pain or pain caused by cancer, rheumatoid arthritis or migraine headache.

* * * * *